United States Patent
Phan et al.

(10) Patent No.: US 6,784,446 B1
(45) Date of Patent: Aug. 31, 2004

(54) RETICLE DEFECT PRINTABILITY VERIFICATION BY RESIST LATENT IMAGE COMPARISON

(75) Inventors: Khoi A. Phan, San Jose, CA (US); Bhanwar Singh, Morgan Hill, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 218 days.

(21) Appl. No.: 10/230,714

(22) Filed: Aug. 29, 2002

(51) Int. Cl.[7] .............................................. G01N 21/86

(52) U.S. Cl. ................................ 250/559.4; 250/559.45

(58) Field of Search ........................ 250/559.4, 559.45, 250/559.44, 559.34; 356/237.4, 237.5, 237.1, 239.3; 382/144, 145, 149

(56) References Cited

U.S. PATENT DOCUMENTS 6,076,465 A * 6/2000 Vacca et al. ................ 101/481

* cited by examiner

Primary Examiner—Que T. Le
(74) Attorney, Agent, or Firm—Amin & Turocy, LLP

(57) ABSTRACT

One aspect of the present invention relates to a system and method for detecting defects on a reticle by inspecting latent images printed on a resist wafer by the reticle. The system includes a wafer having a printed photoresist layer formed thereon, a latent image inspection system connected to the wafer exposure system for examining the printed photoresist layer in order to determine whether a reticle employed to print the photoresist layer is defective, and a processor for receiving data from the inspection system in order to verify the presence of defects on the reticle. The method involves printing a first latent image, a second latent image, and a third latent image on a resist wafer using a reticle, and comparing the three latent images to one another to determine whether the reticle is defective. Comparison of the latent images may be facilitated by employing an optical system programmed to perform such comparisons.

24 Claims, 6 Drawing Sheets

RETICLE DEFECT PRINTABILITY VERIFICATION BY RESIST LATENT IMAGE COMPARISON

TECHNICAL FIELD

The present invention generally relates to processing a semiconductor substrate. In particular, the present invention relates to a system and method for examining a wafer printed by a reticle in order to inspect for defects on the reticle.

BACKGROUND ART

Achieving the objectives of miniaturization and higher packing densities continue to drive the semiconductor manufacturing industry toward improving semiconductor processing in every aspect of the fabrication process. Several factors and variables are involved in the fabrication process. For example, at least one and typically more than one photolithography process may be employed during the fabrication of a semiconductor device. Each factor and variable implemented during fabrication must be considered and improved in order to achieve the higher packing densities and smaller, more precisely formed semiconductor structures.

In general, lithography refers to processes for pattern transfer between various media. It is a technique used for integrated circuit fabrication in which a silicon slice, the wafer, is coated uniformly with a radiation-sensitive film, the photoresist, and an exposing source (such as optical light, X-rays, or an electron beam) illuminates selected areas of the surface through an intervening master template, the photoresist mask, for a particular pattern. The lithographic coating is generally a radiation-sensitized coating suitable for receiving a projected image of the subject pattern. Once the image is projected, it is indelibly formed in the coating. The projected image may be either a negative or a positive of the subject pattern. Exposure of the coating through the photoresist mask causes a chemical transformation in the exposed areas of the coating thereby making the image area either more or less soluble (depending on the coating) in a particular solvent developer. The more soluble areas are removed in the developing process to leave the pattern image in the coating as less soluble polymer. The resulting pattern image in the coating, or layer, may be at least one portion of a semiconductor device that contributes to the overall structure and function of the device.

Because the photoresist is used to form features on the semiconductor devices, the integrity of the photoresist must be maintained throughout the lithography process. That is, any flaw or structural defect which is present on a patterned photoresist may be transferred to underlying layers during a subsequent etch process wherein the photoresist is employed.

Such flaws and/or structural deformities may be caused by a defect-ridden reticle which is used to pattern the photoresist. Reticle defects may be generated by the fabrication process utilized to produce the mask or reticle as well as during subsequent handling and processing. Reticle defects can often lead to repeating defects on a wafer. A repeating defect is a defect that appears in multiple wafers or layers at about the same location. The repeating defect can be an indicator that a reticle has a defect, as opposed to the defect being caused by a one-time contamination problem or by wafer-to-wafer variations.

With the increasing use of advanced reticle enhancement techniques, the effect of defects, even marginal defects, can be magnified when transferred to a wafer. If the photomask or reticle contains defects, even submicron in range, such defects can be transferred to a wafer during exposure. Defects on reticles may cause inaccurate patterns to form on the wafer. In addition, the electrically active regions may not perform as desired, leading to an overall degradation of chip performance.

For example, closed area defects such as malformed or undeveloped edges, corners and lines as well as undesired depressions, dimples, protrusions and pinholes in the layers may adversely affect the performance of the semiconductor. Adverse effects may include increased resistance, decreased capacitance, ineffective insulation between layers and features, and poor conductivity and interconnections between layers and features.

Conventional inspection tools have been developed to detect defects on the reticle. More recently employed inspection systems utilize defect simulation methods to detect repeating defects in reticles. The defect simulation inspection method involves employing an aerial image microscope system to simulate printability on a wafer. This method compares an optical image with a simulated image derived from the original design data and generated with an aerial image microscope system and predicts how features and defects on reticles will print on full flow production wafers.

However, defect simulation comparisons are not as accurate as die-to-die inspections in pinpointing the precise shape and location of the reticle defect. Furthermore, simulated images involve a considerable amount of image processing power. Such automatic image processing instruments often have difficulty detecting particles on substrates that have defect simulation inspection method requires costly instrumentation capable of comparing an actual photomask geometry against an ideal photomask geometry.

Die-to-die methods involve patterning and developing a resist wafer and then performing a wafer inspection by SEM or by optical methods from die to die to check for any repeating defects. Although typical die-to-die methods are preferred for their accuracy, it is a time consuming and rather slow process. Thus, fabrication times undesirably increase, thereby unduly inflating overall production costs and processing inefficiencies.

Therefore, there continues to be an unmet need for a rapid and more accurate process to assess marginal defects on a reticle in order to increase fidelity in pattern transfer and to improve device performance.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention provides a system and method for examining a reticle for defect printability. More specifically, the present invention involves a system and method for inspecting a reticle for marginal defects by comparing latent images printed on a resist wafer. Marginal defects on the reticle may or may not be destructive to the final device structure, however, in order for this determination to be made, it is desirable to locate and qualitatively analyze such defects in a relatively rapid manner. This may be accomplished in part by using the reticle to print latent images onto the resist wafer and then examining the latent images for defects. The latent images are inspected before the resist is developed. Because the resist wafer is not developed, processing time is reduced and the status of the reticle can be more readily determined.

According to one aspect of the present invention, the reticle may have one die pattern. The one die pattern can be printed at least three times on the photoresist layer at three adjacent locations to form three latent images on the photoresist layer. The three latent images may be compared to one another to establish whether the images exhibit measurable differences from one another. Comparison of the three latent images may be optimized by varying the focal height during the printing of each latent image and/or by varying the exposure conditions for each latent image. Because photoresist materials differ in structural and physical properties, bleachable dye may also be employed in order to enhance the contrast between the printed and non-printed areas of the photoresist layer.

According to another aspect of the present invention, the reticle may have more than one die pattern. The die patterns may be similar or different depending on the desired end product device to be made. Inspection of the reticle for defects may be performed in a similar manner as described above.

The comparison between the three latent images assists in pinpointing and verifying the location of a defect on the reticle. In addition, the comparison facilitates determining the severity of the defect(s) on the reticle. If it is determined that the reticle is defective, then it may be discarded or require full verification by developing the wafer for conventional defect inspection. On the contrary, a qualitative analysis of the defects may also reveal that such defects are minor or inconsequential and not likely to affect the structure or operation of the device. In summation, the quality of the reticle may be ascertained without developing the resist wafer, thereby reducing overall processing time and production costs.

DISCLOSURE OF INVENTION

Figure 1:
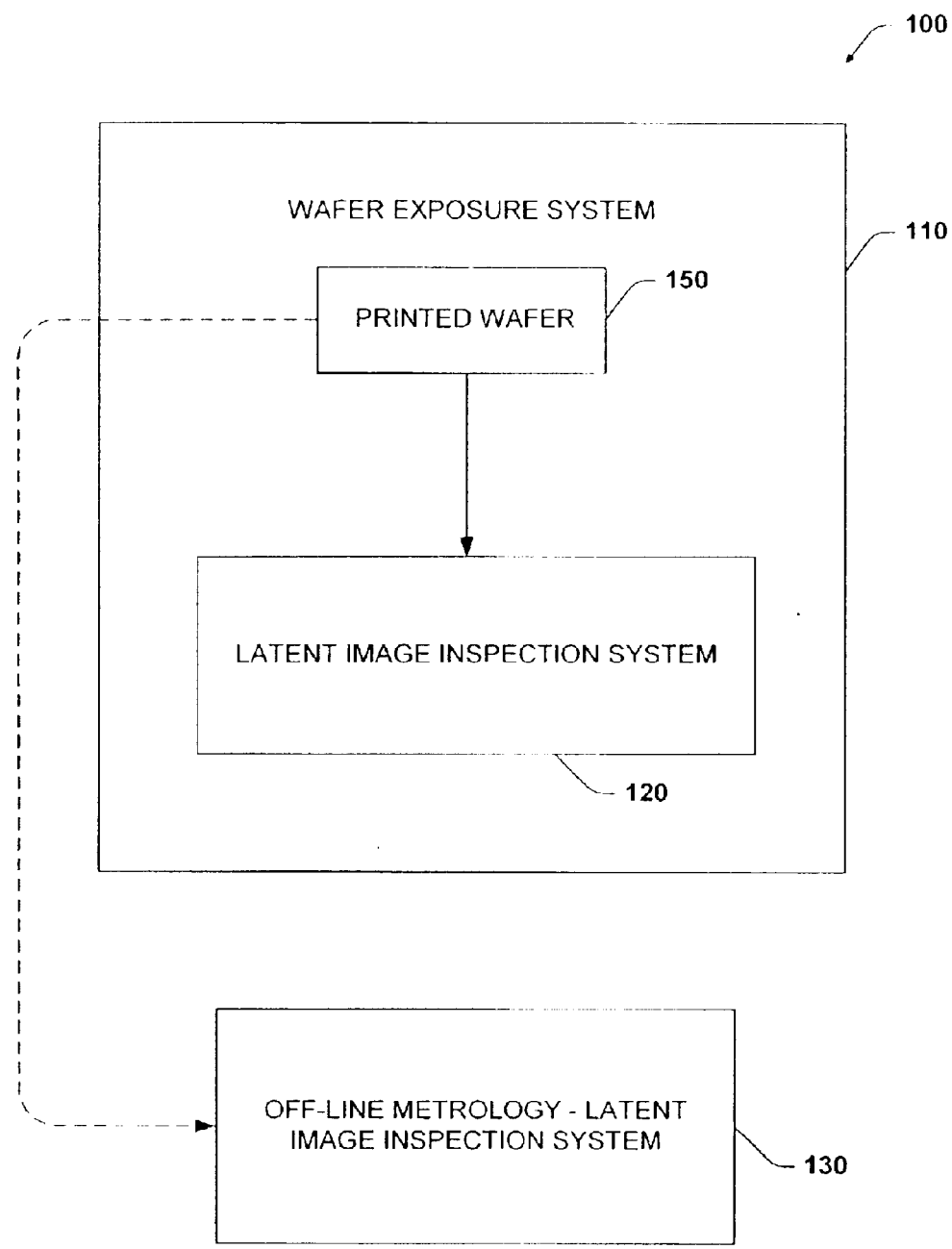
FIG. 1 illustrates a high level schematic block diagram of a system for detecting repeating marginal defects on a reticle in accordance with an aspect of the present invention.

The present invention involves a system and method for examining a reticle for defect printability. More specifically, the present invention provides for a system and method for determining the location, type, and/or severity of marginal defects which may be present on a reticle. The reticle, as described herein, comprises a plurality of similar die patterns which can be transferred to wafers in order to create integrated circuit devices. Each die pattern may be compared to the others for similarities and differences in order to pinpoint irregularities located on the reticle.

According to one aspect of the present invention, one or more than one die pattern on a reticle can be transferred to a resist wafer via a printing process. That is, the resist wafer is printed with at least a first latent image, a second latent image, and a third latent image. The three latent images correspond to the one die pattern (or more than one die pattern) from the reticle. Unlike conventional methods, the printed resist wafer is not developed. Rather, any defects on the printed resist wafer may be detected by examining the latent images on the photoresist layer without developing the resist wafer. Portions of the resist wafer containing the latent images may demonstrate height, width, surface, physical, and/or chemical changes as compared to other (non-exposed) portions of the resist wafer.

By way of example, a reticle may contain six similar die patterns arranged in two rows (e.g., row X and row Y) such that each row has three die patterns. According to the present invention, the die patterns can be printed onto a resist wafer to form latent images. The latent images may then be inspected for defects without developing the resist. Because the six die patterns on the reticle are similar, the latent images within each row may be compared. For example, die X1, X2, and X3 may be printed under variable focal height conditions whereas die Y1, Y2 and Y3 may be printed under variable exposure conditions in order to optimize the comparison of the latent images within each row.

Alternatively, the reticle may contain only a single die pattern. The single die pattern may be printed on the resist wafer six times, thus forming two rows consisting of three latent images in each row. Inspection and comparison of the latent images within each row may be performed as described above.

A bleachable dye may also be applied to the photoresist layer either before or after printing in order to enhance the contrast between the printed and non-printed areas. Thus, a user can more readily and more accurately ascertain the location, quality and type of a marginal defect on a reticle. In doing so, the user can readily determine whether the defect necessitates discarding the reticle. For example, the bleachable dye may be injected into the photoresist layer or portions thereof prior to the printing process. The light used to expose portions of the photoresist layer during the printing process may react with the bleachable dye and in doing so, optimize the contrast between the exposed and unexposed portions of the photoresist layer.

Alternatively, or in addition, a suitable dye may be incorporated into the resist wafer after the printing process is completed such that the dye selectively binds to either the printed or non-printed portions of the resist wafer, depending on the type of dye employed. This may be accomplished in part by exposing the printed resist wafer to vapors of dye under moisture-controlled conditions. The moisture conditions facilitate the incorporation of the dye vapors into either the printed or non-printed portions of the resist wafer.

As previously mentioned, other printing process parameters may be altered or adjusted for each latent image in order to better visualize the latent image and any defects associated therewith. For example, the focal height of the wafer may be varied during the printing of each latent image in order to increase the contrast between latent images (e.g., at least three latent images) in the photoresist. In addition, the latent images may also be inspected at fixed and varied focal heights in order to optimize detection of any defects in the images. For instance, the focal height may fluctuate from low to nominal to high.

Alternatively or in addition, the exposure conditions may also be varied for each latent image printed on the photoresist. For instance, the exposure of light may range from underexposure to nominal exposure to overexposure in such a way that each latent image is printed using an exposure different from the other latent images.

The qualitative analyses of the printed latent images as described above may be facilitated by employing any suitable optical system such as, for example, a scatterometry system, which can be programmed to measure and compare the latent images on the resist wafer. For example, the scatterometry system can be programmed to direct beams of light at various portions of the printed resist wafer. The light reflected from such portions of the printed resist wafer may scatter in different patterns or arrays depending on changes in dimensional or compositional properties resulting from exposure to light during the printing process. The reflected light data for each latent image may be compared to that of another latent image printed on the resist in order to establish the location, type, and severity of the defect as well as its potential effect on the final device. Alternatively, instead of using a scatterometry system, any optical system such as a broadband optical system using 200 to 800 nm light or a spectroscopic system may be employed.

The present invention will now be described in FIGS. 1–8 with respect to a wafer having a photoresist layer formed thereon and a fabricated reticle. For the sake of simplicity, the present invention will be described with respect to printing at least three latent images onto a resist wafer. The three latent images may correspond to either first, second, and third similar die patterns or to a single die pattern on the reticle. However, it should be understood that the reticle may contain a plurality of similar die patterns and thus a plurality of latent images may be printed on the photoresist layer and such is intended to fall within the scope of the present invention. Furthermore, it should be understood that the analysis and/or comparison of latent images may be made die-to-die in the manner described below.

Referring initially to FIG. 1, a high-level, schematic block diagram of a system 100 for examining a reticle for defect printability in accordance with one aspect of the present invention is shown. The system 100 includes a wafer exposure system 110, a latent image inspection system 120, and an optional off-line metrology system 130 for latent image inspection. The wafer exposure system 110 comprises a stepper as well as a light source and may use a series of photoresists and reticles with various desired wavelengths of light in order to form features on a wafer. According to one aspect of the present invention, a reticle (not shown) is used to print at least three latent images onto a resist-clad wafer 150. However, the printed resist wafer 150 is not developed or is not developed until after the reticle undergoes an inspection for defects as described herein.

The wafer exposure system 110 is operatively coupled to the latent image inspection system. That is, the latent image inspection system 120 may be in-line with and/or attached to the wafer exposure system 110, and in particular to the stepper, such that the inspection/comparison of the latent images may occur without re-aligning the wafer. Thus, less time is spent to detect defects on the reticle as compared to conventional methods.

The latent image inspection system 120 comprises a measurement system such as a broadband system, a spectroscopic system, or a scatterometry system, for example, which is programmed to measure the three latent images printed on the resist wafer 150 for an online comparison. The inspection system 120 can analyze the data collected by the scatterometry system in order to determine whether the reticle employed to print the resist wafer has one or more marginal defects thereon.

Alternatively, the latent images may be compared using the off-line latent image inspection system 130. Because this metrology system 130 performs off-line and physically apart from the wafer exposure system, various alignment procedures may be employed in order to properly inspect and compare the latent images to one another. Furthermore, a post-exposure bake process may be performed in a moisture-controlled environment in order to more clearly define the printed areas apart from the non-printed areas on the resist wafer 150.

Figure 2:
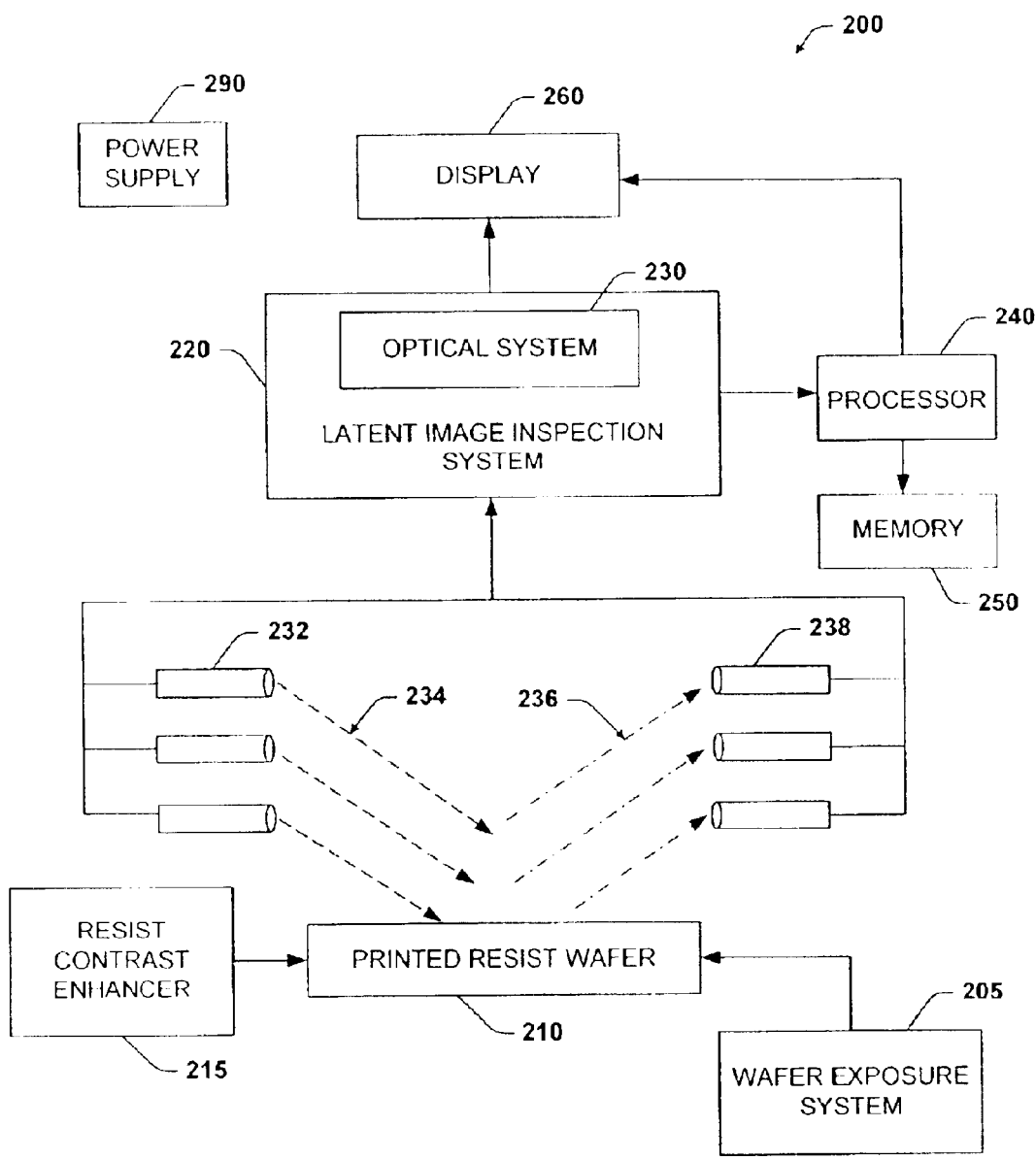
FIG. 2 illustrates a schematic block diagram of a system for detecting repeating marginal defects on a reticle in accordance with an aspect of the present invention.

FIG. 2 is a schematic block diagram of a system 200 for examining a reticle for defect printability in accordance with another aspect of the present invention. The system 200 includes a printed resist wafer 210 which is being inspected for defects. In particular, the resist wafer 210 comprises a wafer having a photoresist layer formed thereover. The photoresist layer may be printed (e.g., patterned) with at least a first, a second, and a third latent image by a wafer exposure system 205 (e.g., reticle and a stepper). In addition, the printed resist wafer may be treated with a contrast enhancing agent 215 such as, for example, a dye. Any suitable dye may be employed to the extent that the dye reacts or binds to either the printed or non-printed portions of the resist in order to enhance the contrast between these portions. Alternatively, or in addition, the resist wafer may be treated with a bleachable dye before being subjected to the printed process to the extent that the dye does not affect the printing process.

As shown in FIG. 2, the printed resist wafer 210 is being examined for defects. In particular, the first, second, and third latent images are being measured by a latent image inspection system 220 to ultimately determine whether the reticle used to form the latent images contains any marginal defects. Such defects may arise randomly as a result of employing the reticle in the printing process.

The inspection system 220 includes an optical system 230 for measuring and comparing the first, second, and third latent images on the wafer 210, and in particular, for pinpointing any changes or differences between them.

More specifically, the optical system 230 may include a broadband system, a spectroscopic system, or a scatterometer having variable grating sizes and pitches. In a series of one or more scans or sweeps of the latent images, the scatterometer directs one or more beams 232 of light 234 at or toward the printed resist wafer 210. The corresponding reflected light 236 is collected by one or more light sensors 238 and then can be analyzed by the inspection system 220 or by an external processor 240.

The three latent images such as A, B and C, for example, are measured by the optical system in order to conduct comparisons among the three latent images to each other. For example, the first comparison may occur between latent images A and B. The second comparison may occur between latent images B and C. Finally, the third comparison may occur between latent images A and C in order to verify or pinpoint the location of the defect.

More specifically, comparing A to B, B to C, and A to C can reveal that a defect is located on at least one of the latent images. Furthermore, performing these three comparisons can verify the location of the defect. For example, if differences between latent images A and B and between latent images B and C are detected but no differences between latent images A and C are detected, then it may be concluded that the defect is located on latent image B which corresponds to die pattern B on the reticle.

The processor 240 receives the reflected light data and performs a number of analyses on the reflected light data in order to ultimately determine whether the reticle is defective, the location of such defects as well as the extent of such defects. Data and information transmitted to or generated by the processor 240 may be stored for future investigation or use in a memory 250.

Information relating to the latent images and to the reticle, can also be communicated to the display 260 in order to allow for further investigation and assessment of the latent images and/or the defects.

A suitable power supply 290 such as a battery may be utilized in order for the system 200 to operate properly.

Figure 3:
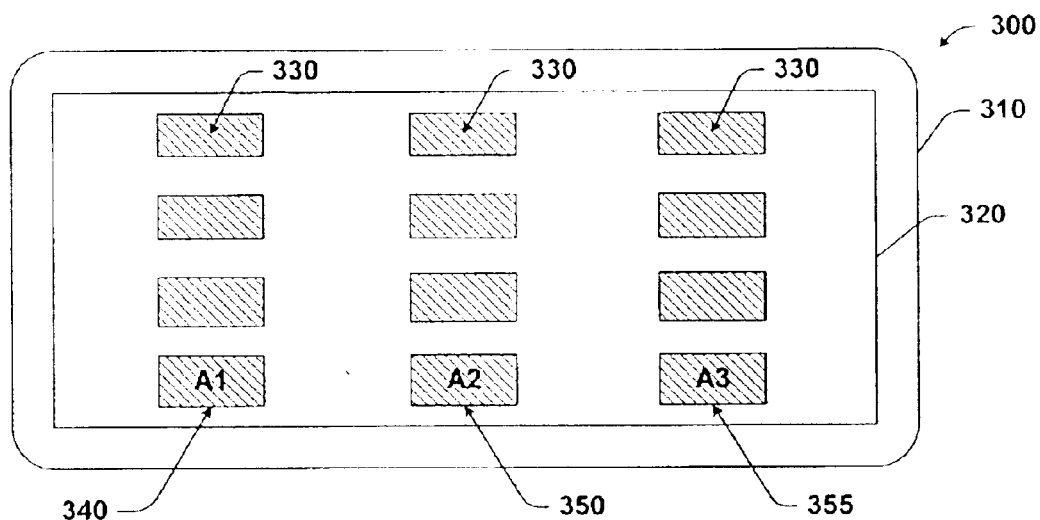
FIG. 3 illustrates a top view of a schematic reticle which may be employed to print a resist wafer in accordance with an aspect of the present invention.

Turning now to FIG. 3, a schematic illustration of a reticle 300 from a top view perspective is shown in accordance with an aspect of the present invention. The reticle 300 comprises a substrate 310 and a chrome layer 320 which has been patterned and developed to form similar die patterns 330. These die patterns 330 can be transferred to a photoresist layer, which is on a wafer (not shown), in order to produce a semiconductor device. For example, a first die pattern A1 340, a second die pattern A2 350, and a third die pattern A3 355 can be printed onto the photoresist layer via a stepper (not shown). The die patterns 330 (including A1 340, A2 350, and A3 355) are repeating images and thus, are substantially similar to each other.

Figure 4:
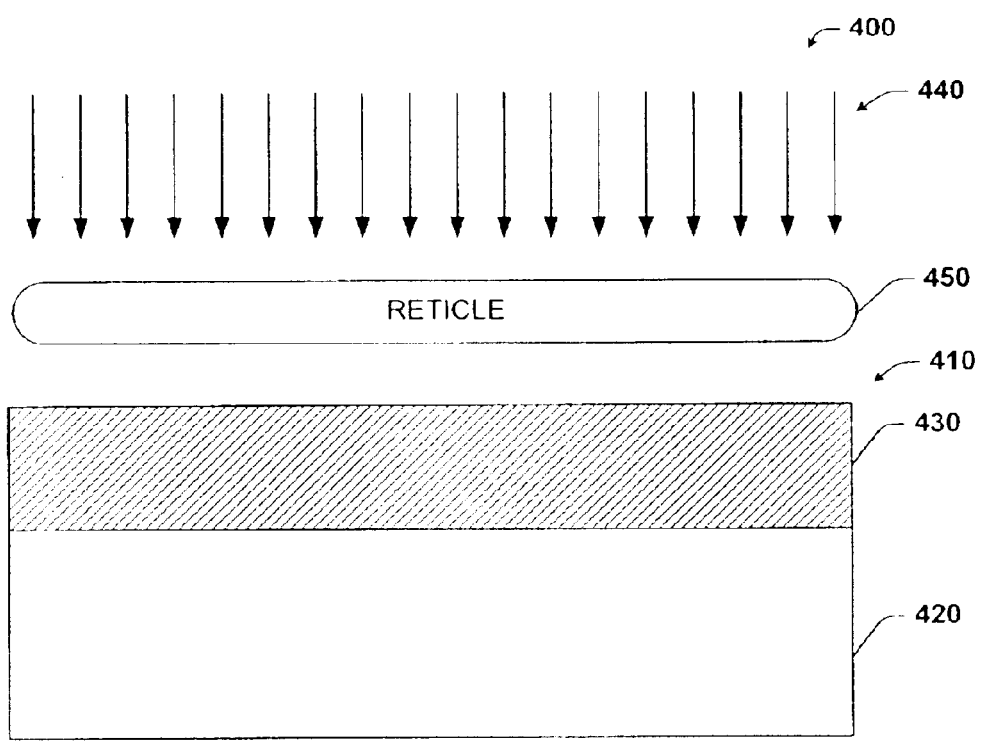
FIG. 4 illustrates a cross-sectional view of a resist wafer undergoing a process in accordance with an aspect of the present invention.

FIG. 4 demonstrates a reticle, which is similar to the reticle 300 described above, being employed in a photoresist printing process 400 in accordance with another aspect of the present invention. As shown in FIG. 4, a resist wafer structure 410 comprises a substrate 420 and a photoresist layer 430 formed over the substrate 420. It should be appreciated that one or more intermediate layers may underlie the photoresist layer 430.

The printing process 400 involves projecting light 440 through openings of a reticle 450 (e.g., similar to the reticle 300 as described above in FIG. 3). In particular, the light 440 is directed through one or more openings of the reticle 450 on to the resist wafer 410 in order to create a printed or latent image on the resist wafer 410, and specifically on the photoresist layer 430. The one or more openings of the reticle 450 correlate to one or more die patterns on the reticle 450. The latent images printed on the resist wafer 410 correspond to the one or more openings of the reticle 450.

Figure 5:
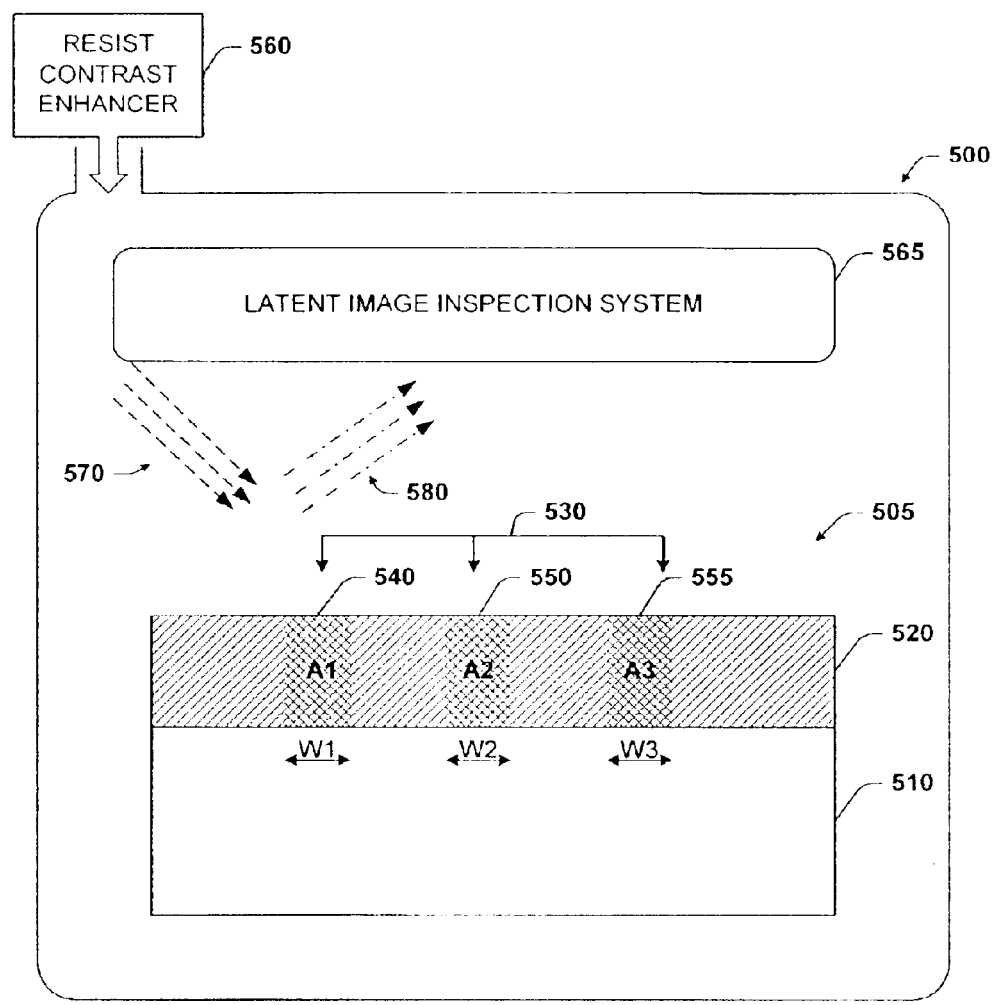
FIG. 5 illustrates a cross-sectional view of a printed resist wafer being inspected for defects in accordance with an aspect of the present invention.

FIG. 5 illustrates a cross-sectional view of a chamber 500 housing a printed resist wafer 505 which may result from a printing process such as that described above in FIG. 4. The resist wafer 505 comprises a substrate 510 and a printed photoresist layer 520 over the substrate 510. The pholoresist layer 520 comprises one or more latent images 530 printed thereon. In particular, a first latent image A1 540, a second latent image A2 550, and a third latent image A3 555 are printed on the photoresist layer 520 via a reticle, such as the reticle 300 (FIG. 3). Thus, the first latent image A1 540 corresponds to the first die pattern A1 340 on the reticle 300. Likewise, the second latent image A2 550 corresponds to the second die pattern A2 350 on the reticle 300, and so on depending on the number of die patterns transferred to and printed on the photoresist layer 520.

In the case of the reticle having only one die pattern, the one die pattern is printed on the photoresist layer at least three times to form at least three latent images. The three latent images may be adjacently located in a row arrangement. More specifically, each of the three latent images may be printed under variable conditions in order to verify the presence of a defect with respect to the die pattern on the reticle. For example, the focal height is varied for each latent image while all other conditions remain constant. Thus, the first latent image is printed using a nominal focal height, the second latent image is printed using a positive focal height and the third latent image is printed using a negative focal height. Alternatively, exposure conditions may be varied while all other conditions remain constant. By way of example, the first latent image is printed with nominal exposure, the second latent image is positive 5% overexposed, and the third latent image is negative 5% underexposed. Moreover, three different exposure fields are formed on the photoresist in order to verify the location of a defect on the reticle.

In order to optimize visualization of the latent images 530 on the resist wafer 505, the contrast of the latent images 530 may be enhanced so as to facilitate inspection and detection of defects in these printed areas. This may be accomplished in part by exposing the printed resist wafer 505 to a resist contrast enhancer 560, such as, for example, vapors of a suitable dye, which can selectively interact and/or bind to either the printed or non-printed portions of the resist wafer.

As previously described, the latent images 530 are compared to one another by a latent image inspection system 565, which can be integrated onto a stepper. The inspection system 565 employs an optical system programmed to qualitatively measure the latent images 530 in order to verify the location of a defect associated with the reticle. In particular, the optical system directs one or more beams of light 570 having a suitable wavelength at the resist wafer 505, and in particular, to the latent images 530 either all at once or in succession as the inspection system 565 moves over the resist wafer 505. The reflected light 580 is collected by the inspection system 565 and then processed or communicated to a processor (e.g., FIG. 2) for further analysis.

For example, the collected data demonstrates that the width dimension W1 of A1 540 substantially matches the width dimension W2 of A2 550. Furthermore, the width dimension W3 of A3 555 substantially matches both A1 and A2. Thus, it may be concluded that based on this assessment, there are no substantial or measurable differences between the three latent images 530. Therefore, it may be concluded that no marginal or gross defects are found or detected at the corresponding die pattern or patterns on the reticle 300 (FIG. 3).

It should be appreciated that a plurality of latent images printed on the photoresist layer may be examined for reticle defects. Alternatively or in addition, the printed image areas may be orderly or randomly selected for inspection to detect marginal defects on the reticle.

Figure 6:
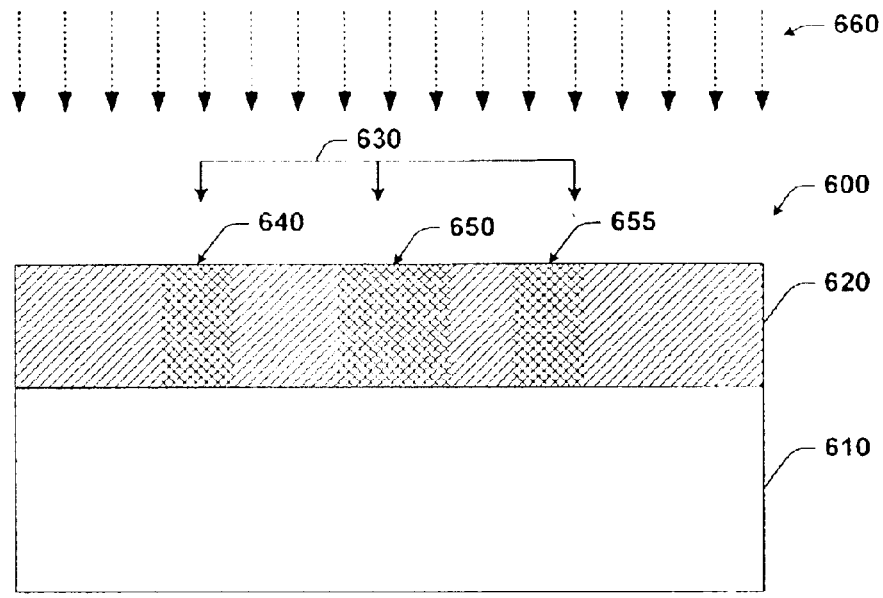
FIG. 6 illustrates a cross-sectional view of a printed resist wafer being treated with a contrast enhancing agent in accordance with an aspect of the present invention.

FIG. 6 illustrates a cross-sectional representation of a printed resist wafer 600 which may also result from a printing process such as that described above in FIG. 4. The resist wafer 600 comprises a substrate 610 and a printed photoresist layer 620 overlying the substrate 610. The photoresist layer 620 comprises at least three latent images 630 printed thereon. In particular, a first latent image 640, a second latent image 650, and a third latent image 655 are printed on the photoresist layer 620 via a reticle, such as the reticle 300 (FIG. 3), and a stepper. The three latent images 630 may correspond to three die patterns on the reticle or to a single die pattern on the reticle.

Before the latent images are inspected for defects, they may be injected or otherwise treated with a contrast enhancing agent such as a bleachable dye as indicated by the dotted arrows 660. The dye is selective to bind to either the printed or non-printed areas on the photoresist layer 620. Therefore, contrast within the photoresist layer 620 is enhanced in order to provide improved visualization of the printed areas (e.g., latent images 630).

Figure 7:
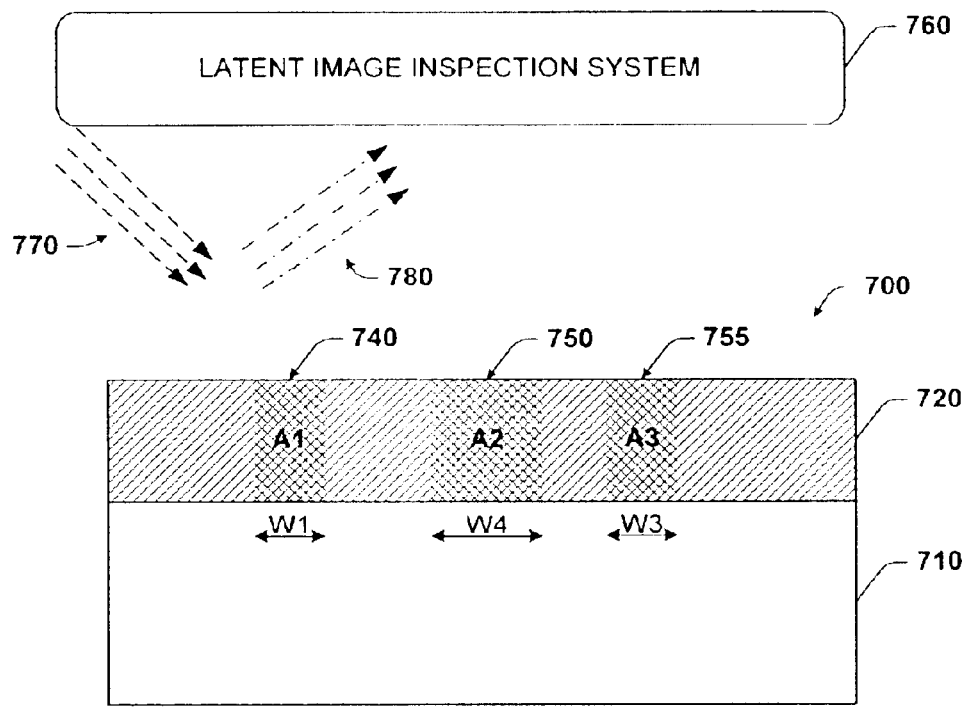
FIG. 7 illustrates a cross-sectional view of a printed resist wafer being inspected for defects in accordance with an aspect of the present invention.

In FIG. 7, a dye-treated, printed resist wafer 700 is illustrated undergoing an inspection process. The resist wafer 700 is similar to the wafer 600 as described in FIG. 6. For example, the resist wafer 700 comprises a substrate 710 and a dye-treated photoresist layer 720. The dye-treated photoresist layer 720 comprises a first latent image A1 740, a second latent image A2 750, and a third latent image A3 755 printed thereon. The latent images may correspond to first die pattern A1, second die pattern A2, and third die pattern A3 of the reticle 300 (FIG. 3), respectively. Alternatively, the latent images 740, 750, 755 may correspond to the same die pattern. It is also contemplated that at least a portion of the printed photoresist layer 720 has been treated with the dye.

The first 740, second 750, and third 755 latent images may be measured by a latent image inspection system 760 in order to detect marginal defects on the corresponding reticle 300. The inspection system 760 may employ a broadband system, a spectroscopic system, or a scatterometry system programmed to measure the dimensions of the latent images. The dimensions of the latent images can be compared in order to ascertain any differences between the latent images.

For example, one or more beams of light 770 having a suitable wavelength are directed at the latent images 740, 750, 755 either all at once or in succession as the inspection system 760 moves across the resist wafer 700. The reflected light 780 is collected by the inspection system 760 and then processed or communicated to a processor (e.g., FIG. 2) for analysis and comparison.

Moreover, the inspection system 760 facilitates verifying whether a random defect has occurred as a result of the reticle by comparing the first 740, second 750, and third 755 latent images on the resist wafer 700 to each other. Because the die patterns 330 on the reticle 300 employed to print the latent images 740, 750, 755 are similar, the latent images 740, 750, 755 should also be similar and/or substantially identical to each other. Any difference between the first 740 and second 750, between the second 750 and third 755, and between the first 740 and third 755 latent images indicates that the reticle is defective at one or more than one die pattern, depending on the results of the comparisons of the latent images.

As can be seen in FIG. 7, the first latent image 740 has a measured width W1, the second latent image 750 has a measured width W4, and the third latent image 755 has a measured width W3. Upon a comparison of the three latent images, comparisons including the second latent image 750 indicate an anomaly, whereas comparisons excluding the second latent image 750 do not indicate the anomaly. Therefore, it can be concluded that the anomaly is due to the second latent image 750. Furthermore, it may be found that the die pattern which corresponds to the second latent image contains the defect.

Such information can be provided by the inspection system 760 and/or by a processor in order to determine the location, type and/or severity of the defect on the reticle.

Examples of possible defects on the reticle include chrome spot, chrome extension, chrome bridging, pin hole, clear extension and clear break. Depending on the location and size of the defect, the defect may be considered to be cosmetic (inconsequential to the overall device), marginal or gross. Gross defects may require that the reticle be discarded, depending on the desired application of the wafer.

Figure 8:
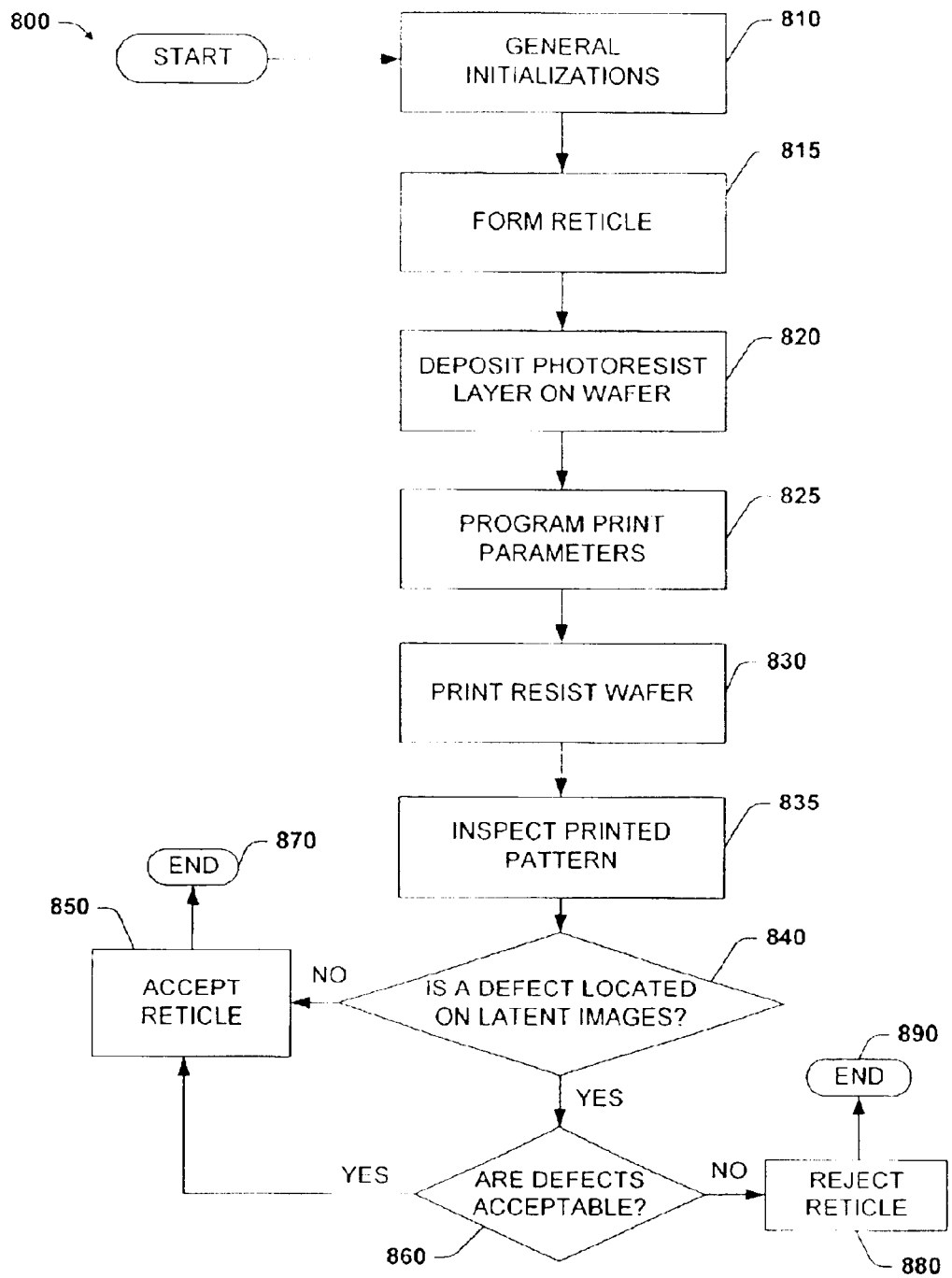
FIG. 8 illustrates a flow diagram of an exemplary method employed in accordance with an aspect the present invention.

Turning now to FIG. 8, is a flow diagram of an exemplary method for inspecting printed resist wafers for defects in order to determine if the reticle is defective. The method primarily begins at 810 with general initializations of the printing and inspection process. The resist wafer may also be prepared for processing.

At 815, a reticle may be fabricated according to the structures which are desired to be formed onto the wafer. The reticle comprises a substrate and a chrome layer formed thereover. Portions of the chrome layer are removed in order to create one or more die patterns on the reticle. The die patterns may be arranged according to the architecture of the desired integrated circuit device, such as for example, a series of rows and columns. In addition, the die patterns may all be similar to each other.

At about 820, a photoresist layer may be formed over the wafer such as by deposition. The printing parameters may be programmed at 825 or earlier if desired. Because the resist wafer is patterned or printed to reveal a latent image but not developed, parameters relating to developing the patterned resist are not necessary to carry out the present invention.

At 830, the resist wafer can be printed by a wafer exposure system using the reticle and a stepper. The printing process involves shining light through one or more portions of the reticle in order to selectively transfer one or more die patterns onto the resist wafer to form at least three latent images on the resist wafer. During the printing process, contrast of the printed as compared to the non-printed areas on the resist wafer may be further enhanced by varying the focal height of the wafer while being exposed to the light from the stepper.

Alternatively or in addition, the printed resist wafer may be treated with a dye agent or dye vapors such that either the printed or the non-printed areas on the resist wafer will selectively interact with and bind to the dye. Enhancing the contrast of the printed or non-printed areas facilitates inspecting and comparing the printed areas or latent images to look for defects. At 835, inspection of the latent images allows a user to examine and verify the defect printability of the reticle. This inspection can be accomplished in part by a latent image inspection system which can either be integrated inline with the stepper or off-line and apart from the wafer exposure system. The latent image inspection system may employ any optical system programmed to measure and compare the latent images in such a way as to allow a qualitative analysis of the latent images to result.

Once the measurements are collected by the inspection system and analyzed, it can be determined whether a defect is located on any of the latent images (at 840). If no defects are detected, then the reticle may be accepted for future and subsequent use at 850. The reticle inspection process ends at 870.

However, if a defect has been located on a latent image, then it can be determined whether the defects are acceptable or severe and destructive to the device at 860. If the defects are not acceptable because they would unduly affect device performance, then the reticle is rejected at 880; and the inspection process terminates at 890 for the present reticle. On the contrary, if the defects are inconsequential and acceptable, the reticle is accepted at 850; and the inspection process ends at 870.

Although the invention has been shown and described with respect to several aspects, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any component which performs the specified function of the described component (ie., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system for examining a reticle for defect printability comprising:
    a wafer exposure system for transferring one or more die patterns from a reticle to a resist wafer to form latent images which correspond to the one or more die patterns,
    wherein the wafer exposure system comprises a latent image inspection system for comparing the latent images to one another in order to verify whether the one or more die patterns are defective.

2. The system of claim 1, wherein the resist wafer comprises a photoresist layer formed over a silicon substrate.

3. The system of claim 1, wherein the latent images comprise at least a first latent image, a least a second latent image, and at least a third latent image.

4. The system of claim 1, further comprising a processor operatively connected to the latent image inspection system for analyzing light data collected by the latent image inspection system to facilitate comparisons between the latent images.

5. The system of claim 1, further comprising a resist contrast enhancing agent for selectively binding to portions of the resist wafer in order to optimize the contrast between printed and non-printed portions of the resist wafer.

6. The system of claim 1, wherein the latent image inspection system utilizes one of a broadband system, a spectroscopic system, or a scatterometry system in order to facilitate verifying the presence of defects on the reticle.

7. The system of claim 5, wherein the resist contrast enhancing agent comprises a bleachable dye.

8. The system of claim 1, wherein the wafer exposure system directs a wavelength of light through one or more openings in the reticle in order to print at least three latent images on the resist wafer such that the latent images printed thereon are not developed prior to inspection by the latent image inspection system.

9. A system for examining a reticle for defect printability comprising:
    a wafer exposure system comprising a resist wafer, the resist wafer comprising a photoresist layer formed over a substrate, the photoresist layer having at least a first latent image, at least a second latent image, and at least a third latent image printed therein;
    a latent image inspection system operatively connected to the wafer exposure system for examining the printed latent images in order to determine whether a reticle employed to print the latent images is defective, the inspection system comprising a measurement system to facilitate comparing the first, second, and third latent images printed on the photoresist layer; and
    a processor for comparing and analyzing data gathered by the inspection system to determine whether at least one of the first, second, and third latent images is defective.

10. The system of claim 9, further comprising a resist contrast enhancing agent for selectively binding to portions of the resist wafer in order to optimize the contrast between printed and non-printed portions of the resist wafer.

11. The system of claim 9, wherein the latent image inspection system utilizes one of a broadband system, a spectroscopic system, or a scatterometry system in order to facilitate verifying the presence of defects on the reticle.

12. The system of claim 10, wherein the resist contrast enhancing agent comprises a bleachable dye.

13. The system of claim 9, wherein the wafer exposure system directs a wavelength of light through one or more openings in a reticle in order to print at least three latent images on the resist wafer such that the latent images printed thereon are not developed prior to inspection by the latent image inspection system.

14. The system of claim 9, wherein the latent image inspection system is positioned in-line with a stepper apparatus.

15. The system of claim 9, wherein the latent image inspection system is positioned as an off-line metrology tool.

16. A method for examining defect printability of a reticle comprising:
    providing a resist wafer comprising a photoresist layer, the photoresist layer being the uppermost layer;
    printing a first latent image, a second latent image, and a third latent image on the photoresist layer using a reticle; and
    analyzing the first latent image, the second latent image, and the third latent image with respect to one another to determine whether the reticle is defective.

17. The method of claim 16, further comprising:
    directing a beam of light at the first, second, and third latent images printed on the resist wafer;
    collecting reflected light data from the first, second, and third latent images; and
    comparing the reflected light data from the first, second, and third latent images to determine whether the reticle employed to print the latent images is defective.

18. The method of claim 16, wherein analyzing the latent images printed on the resist wafer comprises employing an optical system to generate data relating to the appearance of the latent images such that they may be qualitatively compared.

19. The system of claim 16, wherein analyzing the first, second, and third latent images printed on the resist wafer comprises at least three comparisons of the latent images in order to verify a defect location on the reticle, the three comparisons comprising a first comparison between the first and the second latent images, a second comparison between the second and the third latent images, and a third comparison between the first and the third latent images.

20. The method of claim 16, further comprising enhancing the contrastability of the resist wafer to facilitate inspection and comparison of the latent images.

21. The method of claim 20, wherein enhancing the contrastability of the photoresist layer comprises at least one of varying a focal height of the wafer during the printing process, selectively implanting a bleachable dye into at least a portion of the resist wafer, and exposing the printed resist wafer to dye vapors under a controlled, moisture-rich environment.

22. The method of claim 20, wherein the first, second, and third latent images may each be printed on the resist wafer at various focal heights in order to enhance the contrast between the latent images and non-printed areas on the resist wafer.

23. The method of claim 20, wherein the first, second, and third latent images may each be printed on the resist wafer at various exposures, the various exposures comprising a nominal exposure, an underexposure and an overexposure.

24. The method of claim 16, wherein the first latent image, the second latent image, and the third latent image correspond to at least one die pattern on the reticle.

* * * * *